United States Patent
Gustavsson et al.

(10) Patent No.: US 10,729,587 B2
(45) Date of Patent: Aug. 4, 2020

(54) HEARING PROTECTOR AND DATA TRANSMISSION DEVICE

(71) Applicant: HELLBERG SAFETY AB, Stenkullen (SE)

(72) Inventors: Andreas Gustavsson, Stenkullen (SE); Joakim Ohlander, Stenkullen (SE)

(73) Assignee: Hellberg Safety AB, Stenkullen (SE)

( * ) Notice: Subject to any disclaimer, the term of this patent is extended or adjusted under 35 U.S.C. 154(b) by 0 days.

(21) Appl. No.: 16/099,406

(22) PCT Filed: May 5, 2017

(86) PCT No.: PCT/SE2017/050447
§ 371 (c)(1),
(2) Date: Nov. 6, 2018

(87) PCT Pub. No.: WO2017/196231
PCT Pub. Date: Nov. 16, 2017

(65) Prior Publication Data
US 2019/0083320 A1 Mar. 21, 2019

(30) Foreign Application Priority Data
May 11, 2016 (SE) ........................................ 1650634

(51) Int. Cl.
*G10K 11/16* (2006.01)
*A61F 11/06* (2006.01)
(Continued)

(52) U.S. Cl.
CPC .............. *A61F 11/14* (2013.01); *A61F 11/06* (2013.01); *F16P 3/147* (2013.01); *G08B 6/00* (2013.01);
(Continued)

(58) Field of Classification Search
CPC .... A61F 11/14; A61F 2011/145; A61F 11/06; A61F 2250/0002; G08B 6/00;
(Continued)

(56) References Cited

U.S. PATENT DOCUMENTS 6,067,006 A    5/2000   O'Brien
7,512,247 B1 *   3/2009   Odinak ................ H04R 1/1016
                                                          381/312
(Continued)

FOREIGN PATENT DOCUMENTS

DE   102015206608 A1   4/2016
EP       1674062 A1   6/2006
(Continued)

OTHER PUBLICATIONS

International Search Report for Corresponding PCT/SE2017/050447 dated Jun. 13, 2017.
(Continued)

*Primary Examiner* — Ammar T Hamid
(74) *Attorney, Agent, or Firm* — Sandberg Phoenix & von Gontard, P.C.

(57) ABSTRACT

A hearing protector device (9) comprising a controller (11), a memory (14), and a receiver (12) is provided. The controller (11) is configured to be connected to the memory (14), the receiver (12) and an at least one user-notifying device (31) adapted to notify a hearing protector user. The hearing protector device (9) is configured to receive at least one data transmission signal from a data transmission device (20); storing at least one signal parameter; and comparing said data transmission signal to the at least one stored signal parameter. The at least one stored signal parameter is associated with at least one suitable notification; wherein the user-notifying device (31) is configured to, when the signal from the data transmission device (20) matches the signal parameter, present the at least one notification associated to the signal parameter to the hearing protector user. A data transmission device (20) comprising a processor (21) configured to be connected to an external signal receiver (22) and a data device transmitter (23) is also provided, wherein the data transmission device (20) is configured to receive at (Continued)

least one external signal from an external source (40) and transmit a data transmission signal configured to be received by at least one hearing protector device (9).

16 Claims, 5 Drawing Sheets

(51) Int. Cl.
*A61F 11/14* (2006.01)
*G08B 21/02* (2006.01)
*H04R 1/10* (2006.01)
*F16P 3/14* (2006.01)
*G08B 6/00* (2006.01)
*H04R 5/033* (2006.01)
*H04R 5/04* (2006.01)
*G08B 25/00* (2006.01)
*G08B 1/08* (2006.01)

(52) U.S. Cl.
CPC ........... G08B 21/02 (2013.01); H04R 1/1083 (2013.01); *A61F 2011/145* (2013.01); *A61F 2250/0002* (2013.01); *G08B 1/08* (2013.01); *G08B 25/009* (2013.01); *H04R 1/1041* (2013.01); *H04R 5/033* (2013.01); *H04R 5/04* (2013.01); *H04R 2420/07* (2013.01); *H04R 2460/01* (2013.01)

(58) Field of Classification Search
CPC ........ G08B 21/02; G08B 1/08; G08B 25/009; F16P 3/147; H04R 1/1083; H04R 1/1041; H04R 5/033; H04R 5/04; H04R 2420/07; H04R 2460/01
USPC .......................................................... 381/72
See application file for complete search history.

(56) References Cited

U.S. PATENT DOCUMENTS

| | | |
|---|---|---|
| 2008/0144840 A1 | 6/2008 | Goldstein et al. |
| 2008/0189820 A1 | 8/2008 | Duffy et al. |
| 2009/0082071 A1* | 3/2009 | Hicks, III ............ G10K 11/178 455/570 |
| 2011/0006894 A1 | 1/2011 | Witwer et al. |
| 2011/0200214 A1 | 8/2011 | Knox et al. |
| 2012/0033823 A1* | 2/2012 | Rogers .................... A61F 11/08 381/72 |
| 2012/0281863 A1 | 11/2012 | Iwano |
| 2013/0101130 A1* | 4/2013 | Bouhraoua ............. A61F 11/08 381/72 |
| 2015/0071457 A1 | 3/2015 | Burciu |
| 2015/0190284 A1 | 7/2015 | Di Censo et al. |
| 2016/0132046 A1 | 5/2016 | Beoughter et al. |
| 2016/0267925 A1 | 9/2016 | Nomura |

FOREIGN PATENT DOCUMENTS

| | | |
|---|---|---|
| GB | 2456296 A | 7/2009 |
| KR | 101018285 B1 | 3/2011 |
| WO | 2009131518 A1 | 10/2009 |

OTHER PUBLICATIONS

Written Opinion for Corresponding PCT/SE2017/050447 dated Jun. 13, 2017.
Search Report Issued for Corresponding European Patent Application No. 17796485.5 dated Jan. 7, 2020.

* cited by examiner

HEARING PROTECTOR AND DATA TRANSMISSION DEVICE

CROSS-REFERENCE TO RELATED APPLICATIONS

This application is the US National Stage under 35 USC § 375 of, and claims priority to, PCT/SE2017/050447 filed May 5, 2017, which in turn claims priority to Swedish App. No. 1650634-7 filed May 11, 2016. Both of said applications are incorporated herein by reference.

TECHNOLOGY FIELD

Present invention relates to hearing protectors which may be used in industrial environments or in general noisy environments and a data transmission device configured to communicate with said hearing protectors.

BACKGROUND

Hearing protectors are used largely in the industry to protect the worker from environmental noise. Typically, hearing protectors comprise two ear cups positioned over the wearer's ears. The hearing protectors may either be conventional hearing protectors or active noise cancelling hearing protectors. Active noise cancelling hearing protectors are sometimes provided with active elements, such that the passive sound-reducing function is combined with the function of actively reproducing sound inside the ear cup to allow the user to hear this reproduced sound. Such an active element typically includes an electronic unit comprising a speaker and/or one or a plurality of microphones. The active element may incorporate different functions. One type may, for instance, contain a radio receiver and the electronic circuitry required to reproduce sound received by the radio receiver through the speaker. Another type may be designed such that it is capable of reproducing ambient sound from the vicinity of the hearing protector in anti-phase. Still another type may be designed for communication, such as connection by Bluetooth and/or radio link and/or cable, either built into the device or connected to one or a plurality of external units.

The efficient available means for minimizing the exposure to sounds may however result in that the hearing protector user is unable to be aware of the surroundings both audibly and, when the user performs various task demanding full attention, visibly. Thus, various measurements have been taken in the art to provide means to notify a hearing protector user of important events.

US 2008/189820 A1 discloses a protection mask for welding comprising speakers configured to alert the user if a gas leak has been identified in the vicinity or inform the wearer regarding parameters concerning the welding equipment or operation.

EP 1674062 A1 discloses a hearing protector comprising an evaluation unit and a microphone. Specific sound patterns can be loaded into the hearing protector via a wired or wireless interface. When a sound corresponding to a registered sound pattern occurs the hearing protector user is alerted by a speaker in the hearing protector. The alert may comprise of synthetic speech, a predefined sound or a reproduction of the sound pattern in question.

US 2015/0190284 A1 discloses an ear plug with active noise cancellation means comprising a microphone and a unit storing two databases. The first database comprises sounds which should be let through to the ear plug user and the second database comprises sounds which should be eliminated by the active noise cancelling function. The ear plug user can record and allocate new sounds to the databases through buttons on the ear plug. The earplug further comprises a speaker for modifying, enhancing or generating a desired sound to the ear plug user.

SUMMARY

It is in view of the above considerations and others that the various embodiments of the present invention have been made.

One problem today is that the hearing protector user is prevented from hearing audible alarms, alerts, signals and notifications due to the damping by the hearing protectors. Another problem is that a hearing protector device user in some cases is secluded from events in the surrounding area due to his or hers focus on the work at hand, and is therefore unable to see, hear or feel events in the surroundings. In combination with the sound dampening properties of the hearing protector, the hearing protector user may be completely secluded from the surrounding environment.

In a working environment there may be a lot of inaudible information happening in the surrounding working area that the hearing protector user never gets information of unless the he or she stops the work and visually checks the personal equipment or surrounding equipment. There can also be important events in the working area that the worker needs to be aware of for personal safety, for example if a gas sensor in a production facility registers a gas leak or a fire alarm is sprung. Furthermore, in many situations the worker needs to access this information without removing his/her hands or eyes from the tools or working situation. In some cases a user of a machine or a tool may need to be informed regarding deviations, diagnostic parameters etc. concerning said tool or machine without removing hands or eyes from the tool or machine.

Accordingly it is the general object of the invention to distribute notifications regarding relevant information to a hearing protector user without requiring the user to divert the attention from the work at hand further to provide noise cancelling.

Hearing protectors are in many cases worn by several users in a work environment. In some situations several users may not be allowed to hear audible signals over the damping of the hearing protectors or to remove eyes or hands from their work at hand. Hence, there is a need for a more efficient way of distributing information between a plurality of hearing protector users. Accordingly it is a further object of the invention to enable efficient distribution of information amongst a plurality of hearing protector users.

The above objects have therefore been addressed by the independent claims. Advantageous embodiments are defined in the appended dependent claims.

According to a first aspect, a data transmission device and a hearing protector device are provided. The hearing protector device comprises a controller configured to be connected to a memory, a receiver and at least one user-notifying device adapted to notify a hearing protector user. The hearing protector device is configured to receive at least one data transmission signal from the data transmission device. The hearing protector device is also configured for storing at least one signal parameter and comparing said signal to the at least one stored signal parameter. The at least one stored signal parameter is associated with at least one suitable notification, while the user-notifying device is configured to, when the signal from the data transmission device matches the signal parameter, present the at least one notification associated to the signal parameter to the hearing protector user. Said data transmission device comprises a processor configured to be connected to an external signal receiver and a data device transmitter. Also, the data transmission device is further configured to receive at least one external signal from an external source and transmit a data transmission signal configured to be received by at least one hearing protector device. Hence, efficient distribution of information between several hearing protector device users can be achieved. Furthermore, the implementation of a data transmission device as a "hub" for several external sources distributing information via the hearing protector device increases the ability to trace important signals and allows for user-friendly installation.

According to a second aspect, the data transmission device is configured to generate identification data associated with the external signal and/or external source and transmit the data transmission signal comprising the identification data. The hearing protector device is consequently configured to receive the data device signal comprising the identification data associated with at least one external source generating at least one external signal. The identification data enables the external signals to be categorized in terms of originating source and different conditions and states of the originating source. Thus a manner of distributing information regarding different states and conditions of an external device or source to a hearing protector device user is achieved.

A hearing protector device is in many cases used in several different situations, environments and in conjunction with different tools or machines. Accordingly, there is a need for adapting the means of notifying the user as well as the relevant external signals depending on the current environment and work. Since hearing protectors in many cases are worn by workers in an industrial environment the time available for said adaptation is fairly limited.

According to a third aspect, the data transmission device may comprise an inter-linking device. The inter-linking device may be configured to communicatively couple said data transmission device to the at least one second data transmission device configured to receive additional external signals. Thus providing a simple and fast manner of which a hearing protector can be adapted to different use conditions.

The data transmission device may be further configured to identify a signal received by the at least one second data transmission device, when said at least one second data transmission device is communicatively coupled to the data transmission device. Accordingly, one data transmission device may function as a main receiver for the external signals enabling better traceability of the external signals. Thus a system comprising several data transmission devices is made more user-friendly and less complex.

Furthermore, the data transmission device may be further configured to transmit an at least one second data transmission signal originating from the at least one second data transmission device to the hearing protector device. When several data transmission devices and hearing protector devices are involved in one system the increased complexity may negatively impact the user-friendliness of the system as well the ability to track the active signals. Thus, only having one data transmission device transmitting all data provides for a more user-friendly as well as a less complex system.

According to fourth aspect, the hearing protector device is configured to generate, for each successful matching of the data transmission signal and stored signal parameter, signal detection data and to store said signal detection data. The stored signal detection data allows for monitoring of the work environment or devices connected to the data transmission device, thus increasing the possibility of identifying issues in a working area or working equipment connected to the data transmission device. The hearing protector device may further be configured to receive preconfigured notifications and/or signal parameters from an external device. The preconfigured notifications and/or signal parameters enables quick adaptation for a new application of the hearing protector device.

The hearing protector device may further comprise a hearing protector transmitter configured to transfer the signal detection data to an external device. The external device may make the data more accessible and further enhance the possibility of discovering issues in a working area or equipment.

According to a fifth aspect, the data transmission device may be configured to log at least one external signal and generate and store external signal log data in a data transmission device memory. Wherein the data transmission device memory is configured to store said external signal log data and be connected to the processor. The stored external signal log data allows for monitoring of the work environment or devices connected to the data transmission device, thus increasing the possibility of identifying issues in a working area or working equipment connected to the data transmission device. Due to the possibility of having multiple hearing protector devices connected to one data transmission device collecting data the chances of finding issues in a working area or working equipment increases even more.

The data transmission device may be configured to transmit log data of the external signals to an external device. The external device may make the data more accessible and further enhance the possibility of discovering issues in a working area or equipment.

According to a sixth aspect, the hearing protector device and/or data transmission device further comprises at least one sensor adapted to collect data concerning at least one parameter. Hence, at least one further condition in the vicinity of the hearing protector device and/or the data transmission device may be taken into consideration. The information distributed to the hearing protector device user can thus be adapted in accordance with the conditions present for the said hearing protector device user or data transmission device, resulting in an improved capability to present information regarding dynamic conditions to a hearing protector device user. The usage of said sensors may also be used in order to compensate the external signal data or logged data in relation to the conditions present for the hearing protector user or the data transmission device. Thus, the implementation of said sensors may result in increasing the accuracy of the information distributed to the hearing protector user.

According to a seventh aspect, the hearing protector device may comprise a storing switch. Said storing switch may be configured to upon activation enable an active data transmission signal to be stored in the hearing protector device as a stored signal parameter. Adding signal parameters through a storing switch enables the hearing protector device user to quickly adapt the hearing protector device without requiring additional components (such as additional data transmission devices or external devices with preconfigured signal parameters).

Further advantageous embodiments and technical effects will be described in the detailed description.

BRIEF DESCRIPTION OF THE DRAWINGS

The invention will be described in further detail below under reference to the accompanying drawings.

DETAILED DESCRIPTION OF PREFERRED EMBODIMENTS

The present invention will now be described more fully hereinafter. The invention may, however, be embodied in many different forms and should not be construed as limited to embodiments set forth herein; rather, these embodiments are provided by way of example so that this disclosure will be thorough and complete, and will fully convey the scope of the invention to those persons skilled in the art.

Figure 1:
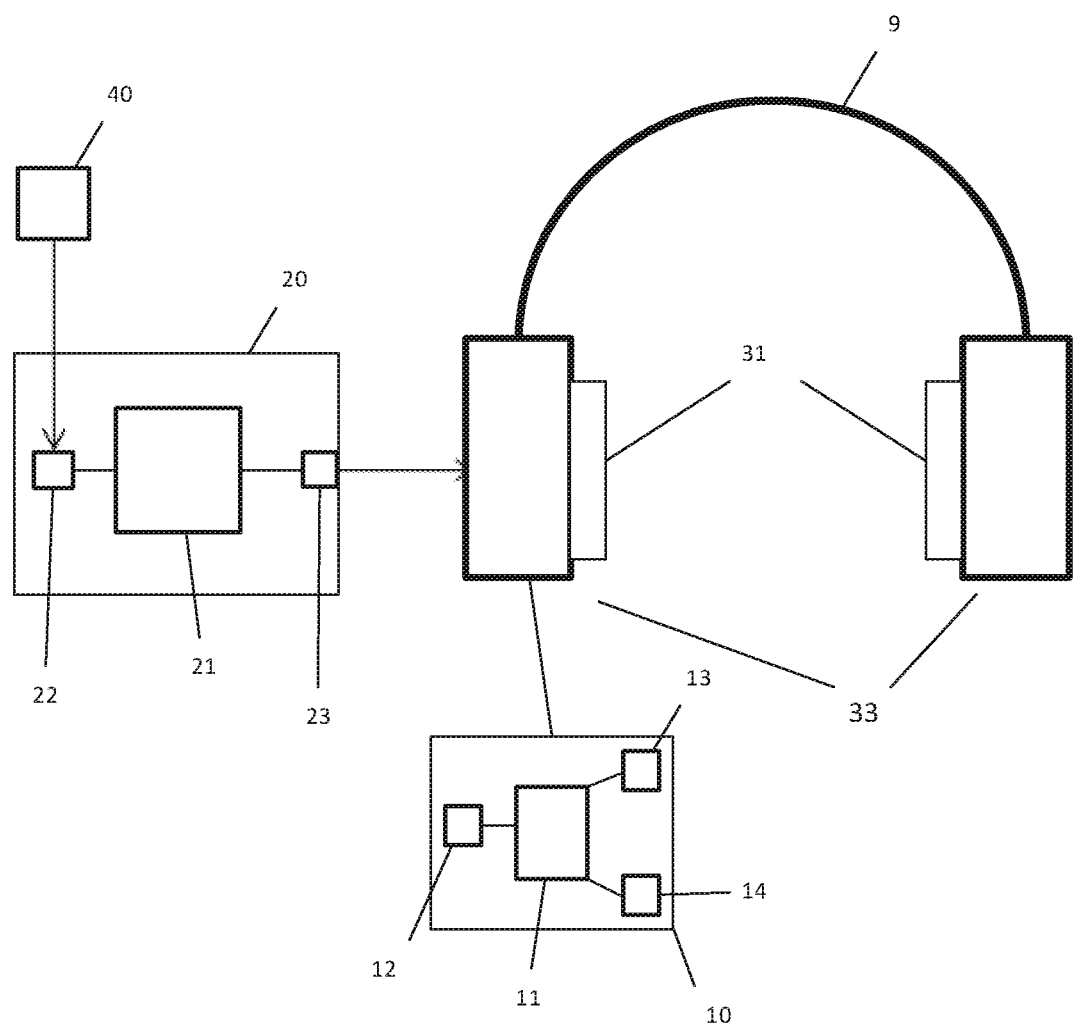
FIG. 1 is a schematic view of the data transmission device and hearing protector device according to an embodiment.

With reference to FIG. 1, a hearing protector 9 and a data transmission device 20 according to an embodiment will be described. The hearing protector comprises a controller 11 configured to be connected to a memory 14, a receiver 12 and at least one user-notifying device 31. The data transmission device comprises a processor 21 configured to be connected to an external signal receiver 22 and a data device transmitter 23.

Said data transmission device 20 may be configured to receive at least one external signal from an external source 40. The data transmission device 20 may be further configured to transmit a data transmission signal configured to be received by at least one hearing protector device 9. Said hearing protector device 9 may be configured to receive the data transmission signal.

The hearing protector device 9 is configured to receive the data transmission signal. The hearing protector device 9 may also store any number of, but at least one signal parameter. Upon identification of an external signal, the external signal is compared to the at least one signal parameter. Preferably, the at least one signal parameter is preconfigured. The signal parameter may be associated with a suitable notification configured to be executed by the user-notifying device 31. Each signal parameter may be associated with a plurality of suitable notifications or vice versa. Accordingly at least one signal parameter is associated with at least one suitable notification. The hearing protector may comprise one or a plurality of, but at least one, user-notifying device 31 configured to, when the data transmission signal matches a signal parameter set, present the at least one associated notification to the hearing protector device user.

The notifications are configured to be presented by the at least one user-notifying device 31. Thus, the notifications may comprise audible or tactile pointers to the hearing protector device which is user configured to give said user an awareness of the surroundings and/or operated tool or machine.

With further reference to FIG. 1, the hearing protector device 9 may comprise two ear protecting elements 33. Preferably, the at least one user-notifying device 31 may be situated inside at least one of the ear protecting elements 31.

The hearing protector device 9 may be of an "over the ear-", "on the ear-" or "in the ear-" type for industrial or professional use. Preferably, the hearing protector device 9 has a regulatory approved passive attenuation giving a specified SNR (Single Number rating) or NRR (Noise Reduction Rating), as would be recognized by one skilled in the art. NRR is a rating based on how much the overall noise level is reduced by a hearing protector, while SNR uses different test frequencies and further takes into account frequency of the noise in the relevant noise environments. Accordingly, the hearing protector device may have a NRR-rating of above 20 dB and accordingly enable a noise reduction of at least 6.5 dB. Preferably, the hearing protector device may for example follow EN 352, ANSI S3.17-1974, AS/NZS 1270:2002 or applicable hearing protector standards relevant in different jurisdictions and countries.

The hearing protector device may also comprise at least one rechargeable or non-rechargeable battery as a power source. Advantageously, the hearing protector device may further comprise any of the following: display for user information and different tactile switches and knobs for user operating. Thus, a more user-friendly hearing protector device is achieved.

The external signal received by the data transmission device may for example be a sensor signal originating from an external sensor. The external sensor may be of any type, configured for any sensory, for example acoustic, sound, vibration, chemical properties, machine diagnostics, electrical current, potential, magnetic, radio, flow, fluid velocity, ionization radiation, navigation, position, angle, displacement, distance, speed, acceleration, optical, light, imaging, pressure, force, density, level, thermal, heat, temperature, proximity, presence etc. In some cases, the sensor signal may be collected from a machine, tool or vehicle existing communicator interface for example CAN, RS485, RS232 etc.

The external signal may be transferred to the external signal receiver 12 through any conventional signal transferring means. Such means may for example be a wired or a wireless connection. Examples on a wireless connection may be Bluetooth, Wi-Fi, radio or a mobile data network.

The data transmission signal generated by the data transmission device 20 to hearing protector device 9 may be transferred through any conventional signal transferring means. Such means may for example be a wired or a wireless connection. Examples on a wireless connection may be Bluetooth, Wi-Fi, radio or a mobile data network.

According to one example of the first embodiment a hearing protector device user is notified of an activated fire alarm. The fire alarm is picked up by a sound sensor, i.e. a microphone communicating with the data transmission device 20. The data transmission device 20 may then distribute the fire alarm signal to the hearing protector device 9 as a data device signal. The data device signal matches with a stored signal parameter and a suitable notification is executed by the at least one user-notifying device 31, notifying the hearing protector device user of the fire alarm.

According to a second embodiment the data transmission device 20 may be configured to generate identification data associated with the external signal and/or external source 40. The data transmission device may then transmit a data transmission signal comprising the identification data. In one example of said embodiment, the external signal received by the data transmission device 20 can be sent to the processor 21 which may be configured to receive and identify said external signal. Furthermore, the data transmission device 20 may also be configured to generate identification data associated with the identified external signal. Such identification data may comprise a unique external data ID associated with a specific external source and/or signal. Preferably, a transmission device memory 24 may be configured to store preconfigured data regarding the external signals and/or external sources configured to transmit external signals to the data receiver 22. The controller 11 may be further configured to generate the data transmission signal, which may comprise of the identification data generated by the data transmission device 20.

In said embodiment the hearing protector device 9 may be configured to receive the data device signal. Said data device signal may comprise the identification data associated with at least one external source generating at least one external signal which the data transmission device 20 is configured to receive, wherein said data device signal is generated by the data transmission device 20. Hence, a user-friendly manner of extracting data regarding specific external sources is achieved both for the hearing protector device 9 and the data transmission device 20. Also, it enables tracking of specific devices and/or signals. Furthermore, notifications based on the external source and the signals originating from the original source can be achieved. Hence, not only an external source may be recognized and identified in the notifications received by the hearing protector device user but several signals associated with different states of the external source may be recognized and identified as well. Thus the notifications may be adapted to notify the user of specific signals associated with specific devices.

The controller 11 is configured to be connected to the memory 14, said memory 14 may be configured to contain a database for storing relevant parameters. Said controller 11 may have a CPU (Central Processing Unit) for calculation of signal parameters and event driven decisions. Hence, the computing may take place without accessing a terminal or external computing device leading to a faster and more robust warning or notification system. The controller may further comprise one or a plurality of a several analog to digital converters for sensor readings and measurement of different signal parameters relevant for the invention.

The controller 11 may further comprise one or a plurality of digital to analog converters configured to generate signal parameters relevant to the invention, whereby the controller 11 may further comprise a communication interface. Hence, the controller may comprise any type of communication interface and function relevant to the invention, as would be recognized by a person skilled in the art.

Figure 2:
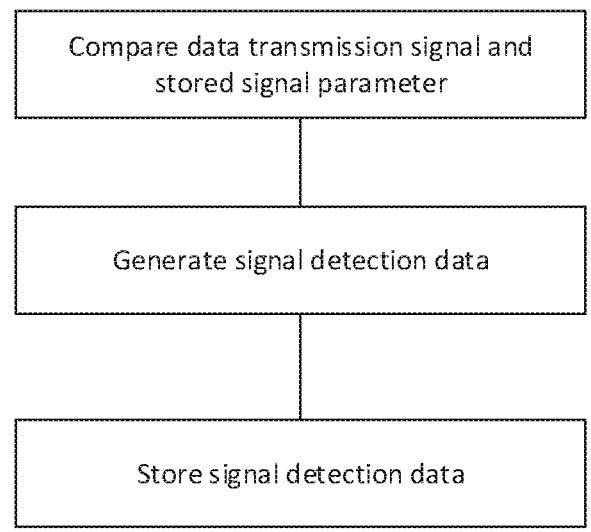
FIG. 2 is a schematic view of the operation performed by the hearing protector device according to another embodiment.

Referring to FIG. 2 the hearing protector device 9 of the second embodiment may be configured to for each successful matching generate signal detection data. Said signal detection data may then be stored in the hearing protector, preferably but not necessarily in the memory 14. The controller 11 may be configured to communicate with said memory 14. Furthermore, as the controller 11 may be configured to match the at least one data transmission signal to the at least one stored signal parameter. The storing of the signal detection data enables traceability of past external signals. The signal detection data may comprise log data for each successful matching and a unique data ID for each identified and matched data transmission signal.

In addition to comprising information regarding occurring events, the generated signal detection data may, according to one embodiment further comprise information associated with the data transmission signal. Such information may include data regarding the external source for example error codes of a machine or tool configured to communicate with the data transmission device, information regarding which device is the source of the signal.

Figure 3:
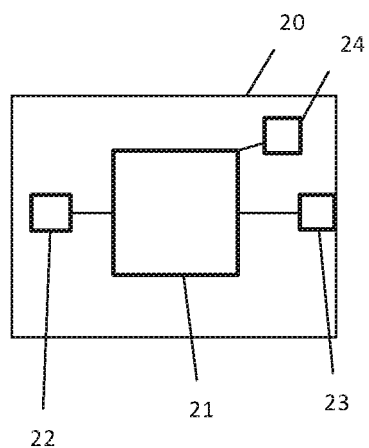
FIG. 3 is a schematic view of the data transmission device according to a further embodiment.

According to a further embodiment depicted in FIG. 3 the data transmission device may be further configured to log the at least one external signal and generate and store the external signal log data. Advantageously, the processor 21 may be configured to log, generate and store the external signal. In an alternative, also advantageous, embodiment the processor 21 may be configured to generate the external signal log data and the data transmission device 20 may further comprise a data transmission device memory 24 configured for storing the external signal log data. The data transmission device memory 24 may be configured to communicate with the processor 21.

Figure 4:
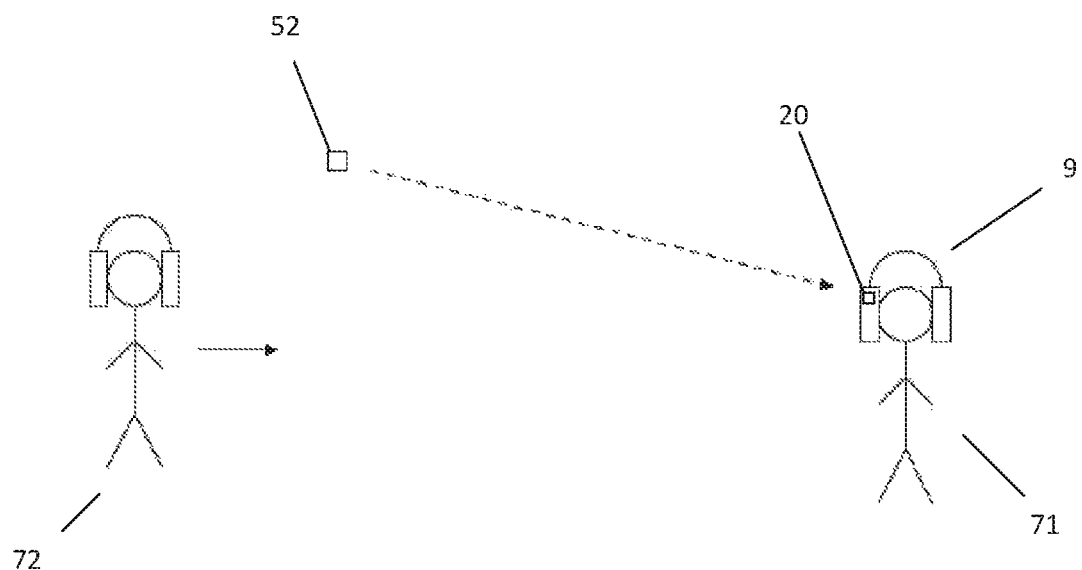
FIG. 4 is a schematic view of an exemplary use case of the hearing protector device and the data transmission device involving proximity detection.

FIG. 4, discloses an example of a use case of present data transmission device 20 and a hearing protector device 9. An area motion detector 52 is connected to the data transmission device 20. A worker 71 wearing a hearing protector device 9, i.e. a hearing protector device user, is occupied with hands and eyes on the work at hand. A second worker 72 approaches the worker 71 and enters the sensors detecting area. The worker 71 then receives a notification, indicating that someone is approaching the area. Hence, the workers 71 awareness of the surrounding area increases. Furthermore, said awareness increases without forcing the worker 71 to lose eye sight of the work at hand.

If the second worker 72 in the current use case example also wears a hearing protector device connected to the data transmission device 20 he or she may be able to receive a notification indicating that he or she approaches the worker 71. Such notification may be useful if the second worker 72 is outside the field of vision of the worker 71, for example around or corner or behind the worker 71.

In some applications it may be preferable for the hearing protector device 9 to comprise more than one user-notifying device 31 configured to be operated independently of each other. Such applications may include, but not be limited to tracking of a moving object or proximity sensory. It may be advantageous during usage of the hearing protector device 9 in said applications to for example "sweep" the sound according to the location of a moving object or person in the vicinity of hearing protector device user. For example a vehicle moving closer to the hearing protector user in a certain direction may prompt a notification by a user-notifying device 31 corresponding to said direction, thus for example not activating a user-notifying device 31 not corresponding to the direction in question.

User-notifying devices may come in different forms. According to one example the user notifying device 31 may comprise a speaker. The speaker may be adapted to send notifications to the hearing protector user in the form of audio. Audio notifications sent to the hearing protector user may include but not be limited to prerecorded sound patterns or synthetic speech.

According to an alternative example, the user-notifying device 31 may comprise a tactile device. The tactile device may be adapted to send notifications to the hearing protector user in the form of tactile signals.

According to one embodiment, the hearing protector device 9 may be configured to receive preconfigured data from an external device such as for example, and without limitation, a computer or a hand held device such as a smart phone, PDA or tablet. The data may preferably comprise preconfigured notifications or signal parameters or both. Said data may be transferred to the hearing protector device 9 through any conventional data transferring means. Such means may for example be a wired or a wireless connection. Examples on a wireless connection may be Bluetooth, Wi-Fi or a mobile data network. The transfer may occur between the external device and the receiver 12 which may be configured to receive preconfigured data from the external device or between the external device and an external device port configured to communicatively couple the external device and the controller 11. With regards to the latter option the hearing protector device 9 may further comprise the external device port.

According to another embodiment the hearing protector comprises a hearing protector device transmitter 13 connected to the controller 11. Said hearing protector device transmitter 13 may be configured to transfer the signal detection data to an external device. An external device may in this case be a computer or a hand held network connected device such as a tablet, smart phone or PDA. The signal detection data may be transferred to the external device through any conventional data transferring means. Such means may for example be a wired or a wireless connection. Examples on a wireless connection may be Bluetooth, Wi-Fi or a mobile data network.

Accordingly, the controller may comprise of one or several analog to digital converters for generating a transmittable signal from for example the readings of the sensor of the hearing protector device. The controller 11 may further comprise any known communication interface and function relevant to present invention, as would be recognized by one skilled in the art.

The external device may with reference to said embodiment be configured to store and present the signal detection data. According to one example the stored data may be stored, categorized and presented in a program. Said program may be used for further analysis of the collected data by for example production mangers, service department, the workers using the hearing protectors etc. Such program may be configured to, but not limited to, for example give information of safety critical events in a working area, error codes in machines connected to the data transmission devices etc. Accordingly the program may give the information allowing preventive work improving the safety of the working area or identification of deviations.

According to another embodiment the data transmission device 20 may be configured to transmit log data of the external signals to an external device. An external device may in this case be a computer or a hand held network connected device such as a tablet, smart phone or PDA. The log data may be transferred to the external device through any conventional data transferring means. Such means may for example be a wired or a wireless connection. Examples of a wireless connection may be Bluetooth, Wi-Fi or a mobile data network. The transmission may be performed by the data device transmitter or by a separate unit such as a data transmission device external port configured to communicate with the processor 21.

Similar to the case of the previous example the external device may with reference to said embodiment be configured to store and present the log data. According to one example the stored data may be stored, categorized and presented in a program. Said program may be used for further analysis of the collected data by for example production mangers, service department, the workers using the hearing protectors etc. Such program may be configured to, but not limited to, for example give information of safety critical events in a working area, error codes in machines connected to the data transmission devices etc. Accordingly the program may give the information allowing preventive work improving the safety of the working area or identification of deviations.

Figure 5:
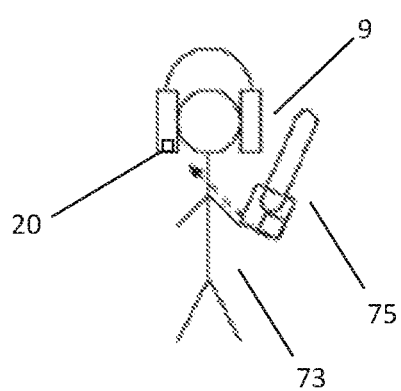
FIG. 5 is a schematic view of an exemplary use case of the hearing protector device and the data transmission device involving notifications regarding machine data of a tool.

FIG. 5 shows an exemplary use case involving a tool user 73 wearing a hearing protector device 9. A plurality of sensors configured for capturing machine data regarding the tool 75 are connected to the data transmission device 20. The tool user 73 may receive notifications regarding different machine parameters through the sensors for capturing machine data, such as machine related functions, status of machine related functions, error codes etc. Thus, the tool user 73 will receive important information regarding the machine used without requiring a pausing of the work at hand or taking the eyes away from the work at hand towards the machine itself. The presentation of the information in notifications according to the example at hand may be particularly advantageous in use cases where the worker operation has to constantly observe the work piece for safety purposes. Such an operation may be for example using a chain saw for cutting down a tree. According to a further embodiment of present invention applied in said use case, the data transmission device or/and hearing protector device 9 may be configured to log and store the collected information associated with the machine. Said information may then be extracted later on for further analysis, which could enable for example identification and tracking of deviations, machine diagnosis, basis for work environment improvement etc. The information can be made even more accessible by transfer to a computer or hand held device and presentation in a graphical interface.

In a further embodiment, the hearing protector device 9 may be a hearing protector with active noise cancelling means, i.e. an active noise cancelling hearing protector. Commonly, noise cancelling means include means of which ambient noise is captured by a microphone to be reproduced by a speaker in the hearing protector in anti phase, thus achieving destructive interference cancelling out the unwanted ambient noise. According to present example the hearing protector device 9 may be further configured to accentuate the notifications. This may be achieved by having the noise cancelling mean being configured to communicate with the controller 11. Accentuation of the notifications may include increasing or decreasing the level of noise cancelling to increase the audibility of a sound notification. The accentuation may also include decreasing the level of noise cancelling in order to reduce resulting vibrations interfering with a notification in the form of a tactile signal.

In some cases the hearing protector device 9 may be equipped with media playing functionality by further comprising a media playing device. The hearing protector device 9 may thus be able to play media files or radio. According to an embodiment the media playing device may be configured to communicate with the controller 11 and accentuate the notifications by for example lowering the volume of the media currently playing or even disallow all media playing while a certain notification is active.

In an additional embodiment, the data transmission device 20 may be further configured to encrypt the data transmission signal before transmitting the signal to hearing protector device 9. Hence, the information transfer between data transmission device and the at least one hearing protector device 9 can be made secure. A secure information transfer may be crucial in certain applications wherein the data transmission device may be configured to transmit data of a sensitive nature or for making sure that the correct data is transmitted to the correct hearing protector (i.e. the hearing protector with the correct decryption key). The hearing protector device 9 receiving the encrypted may then be configured to receive and decrypt said data. Preferably, the processor 21 of the data transmission device may be configured to encrypt the data transmission signal. Typically, but not necessarily the hearing protector controller 11 may be configured to encrypt said data transmission signal.

Figure 6:
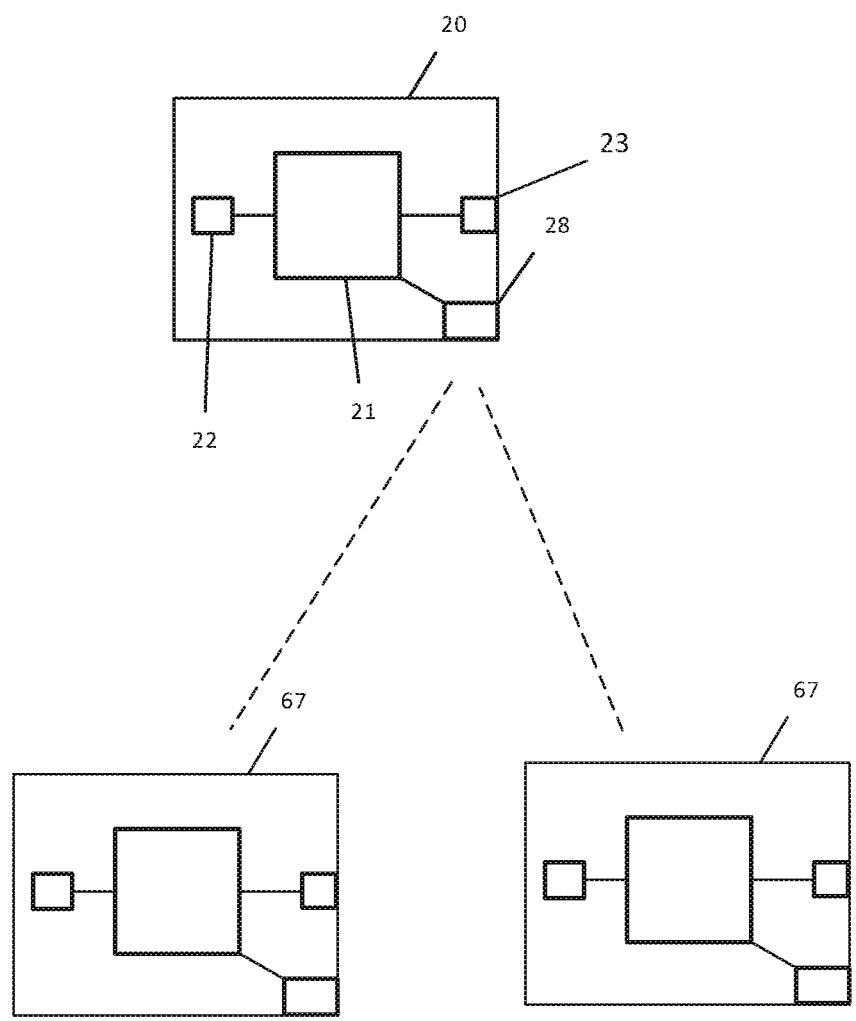
FIG. 6 is a schematic view an embodiment comprising a plurality of data transmission devices.

FIG. 6 shows an exemplified embodiment of the data transmission device 20. According to this embodiment the data transmission device 20 may further comprise an inter-linking device 28 configured to communicate with the processor 21. As seen in FIG. 6, the inter-linking device 28 may be configured to communicatively couple the data transmission device 20 with one or several, but at least one, second data transmission device 67. Preferably, the at least one second data transmission device 67 may be configured to receive additional external signals. The data transmission devices may be coupled via the inter-linking device 28 through any conventional signal transferring means. Such means may for example be a wired or a wireless connection. Examples on a wireless connection may be Bluetooth, Wi-Fi, radio or a mobile data network.

By being connected to one or multiple other data transmission devices the data transmission device 20 may increase the range of external signals identifiable. Accordingly, it would be possible for the hearing protector device user to quickly adapt the hearing protector device for a different work environment by for example coupling additional data transmission devices to the data transmission device in a modular manner.

In another example, when connected to at least one other data transmission device 20 the data transmission device 20 may be configured to identify a signal received by the at least one other data transmission device 20.

Optionally, the data transmission device 20 may be configured to, when communicatively coupled to at least one other data transmission device 20 transmit the data transmission signals generated by the other data transmission devices. The data transmission device 20 may in such an arrangement be configured to function as a transmitter for the data transmission signals generated by the other data transmission devices.

According to an additional embodiment, only the data transmission device 20 is configured to transmit a data transmission signal to the hearing protector device 9. In such an embodiment the data transmission device 20 may function as a "broadcasting unit" intended for providing all of the transmission of data to the at least one hearing protector device 9. When several data transmission devices and hearing protector devices are involved in one system the increased complexity may negatively impact the user-friendliness of the system as well the ability to track the active signals. Thus, only having one data transmission device transmitting all data transmission data may be advantageous.

In some embodiments, the hearing protector device 9 or the data transmission device 20 or both the data transmission device 20 and the hearing protector device 9 may comprise at least one sensor 56. Said sensor may be configured to collect data concerning at least one parameter. The hearing protector device 9 comprising the at least one sensor may be further configured to combine the data collected from the at least sensor and the data transmission signal. The hearing protector device 9 may further comprise at least one analog to digital converter to convert the sensor readings to a signal parameter.

Thereby, the data transmitted in the data transmission signal can be contextualized or adapted in relation to additional parameters taken into consideration through the at least one sensor. Advantageously, such adaptation may be preferable when the hearing protector or data transmission device is used in a dynamic environment with local changes in conditions, for environmental logging or for temperature or pressure compensation.

The sensor 56 may be configured to collect data concerning any conventional parameter. Such a parameter may be for example temperature, proximity, motion, position, tilt etc.

As stated above the hearing protector device may comprise at least one sensor 56. Said sensor 56 may be configured to communicate with the controller 11. Preferably, the controller 11 may be configured to combine the data collected from the at least one sensor 56 and the data transmission signal.

According to one aspect of present embodiment the notification may be adapted in relation to the collected sensor data. Such adaptation may be for example increasing or decreasing the volume or strength of the notification if an object approaches or distances or adapting the signal depending on the position of the hearing protector device 9 or the data transmission device 20.

According to a further embodiment the data transmission device 20 may comprise at least one sensor 56 configured to communicate with the processor 21. Said sensor may be adapted to collect data concerning at least one parameter.

Thereby, the data in the external signal can be contextualized or adapted in relation to additional parameters taken into consideration through the at least one sensor before being transferred to the hearing protector device 9 as a data transmission signal. Advantageously, the data transmission device 20 may be configured to combine the data collected from the at least one sensor 56 and the external signal data and adapt the data transmission signal based on said combination. Such adaptation may be preferable when the data transmission device 20 is used in a dynamic environment or for environmental logging or for compensating for at least one additional parameter thus achieving more accurate data to be transferred or extracted. Preferably, but not necessarily, the processor 21 may be configured to combine the data collected from the at least one sensor and the data transmission signal.

Figure 7:
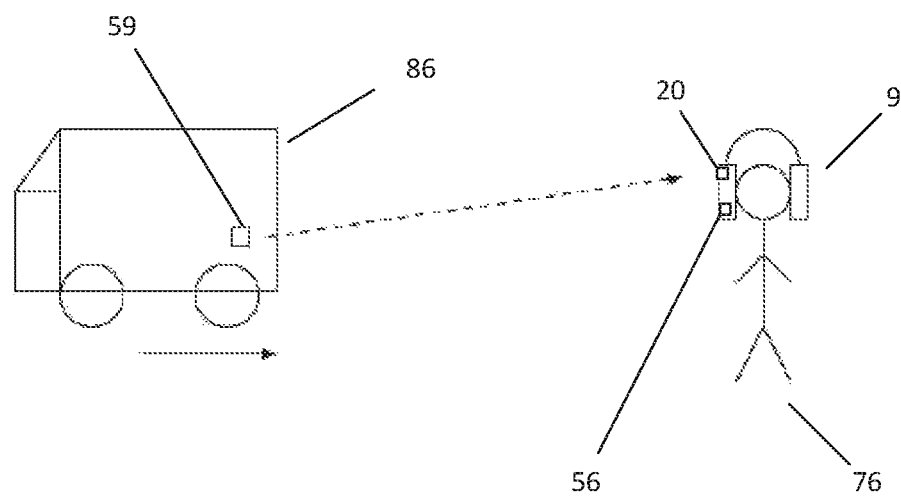
FIG. 7 is a schematic view of an exemplary use case of the hearing protector device and the data transmission device involving a reversing vehicle.

FIG. 7 depicts an exemplary use case involving a reversing vehicle 86, a hearing protector user 76, wearing a hearing protector device 9 and a data transmission device 20. In this use case either the hearing protector device 9 or the data transmission device 20 may comprise a sensor 56 configured to register the position of the hearing protector device 9 or the data transmission device 20. The data transmission device 20 may be configured to receive a signal originating from a vehicle sensor 59 indicating that the vehicle 86 will reverse, for example via the CAN-bus of the vehicle. Depending on the position of the hearing protector device 9 or the data transmission device 20 the notification intended to notify the hearing protector user 76 of the approaching vehicle may be adapted. For example, if the hearing protector device 9 or the data transmission device 20 is deemed to be located within the path of the reversing vehicle 86 the hearing protector user may receive an adapted notification compared to a situation where the data transmission device 20 is outside the path of the reversing vehicle 86.

Figure 8:
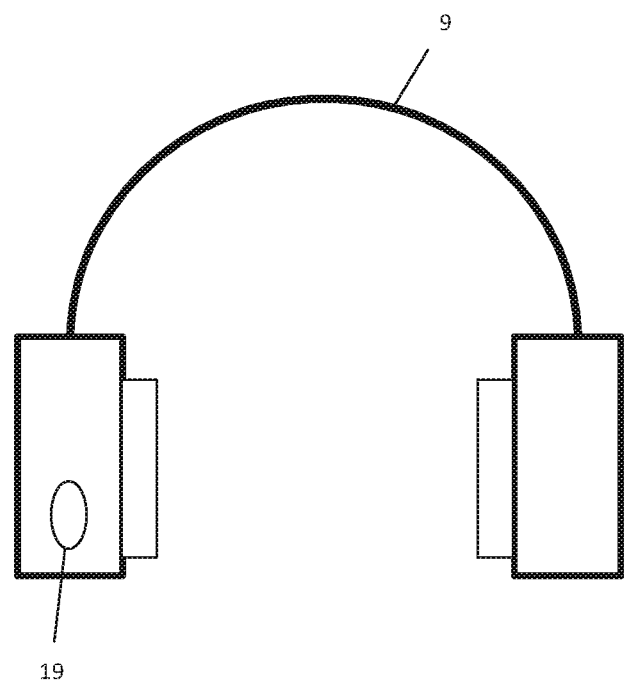
FIG. 8 is a schematic view of an embodiment comprising a storing switch.

As depicted in FIG. 8 the hearing protector device 9 may comprise a storing switch 19 communicatively coupled to the controller 11 and receiver 12. Said storing switch may be configured to upon activation enable an active data transmission signal to be stored. The active data transmission data signal may preferably be stored as a preconfigured signal parameter. Said signal may according to an alternative embodiment be stored in the memory 14. By providing a storing switch 19 it is made possible to allow the hearing protector user to quickly "record" an active data transmission signal and to adapt the hearing protector device 9 to recognize the particular active data transmission signal later on. To exemplify, a user may notice an active error code on a machine or a tool yet to be implemented in the hearing protector signal parameters. The data transmission device connected to the machine or tool may then transfer a data transmission signal to the hearing protector device 9. By activation of the storing switch 19 the parameters associated with the data transmission signal may be stored as preconfigured signal parameters in the hearing protector device 9.

According to one embodiment the data transmission device 20 may comprise a signal-identification switch. The signal switch may be configured to upon activation enable a previously non-identified active external signal to be identifiable. Preferably, but not necessarily the data regarding the previously non-identified external signal maybe stored in the data transmission device memory 24.

According to some embodiments the data transmission device 20 may be configured to be interchangeable. Accordingly it is enabled for the hearing protector user to exchange the data transmission device 20 for another data transmission device 20. By performing the exchange a quick alteration of the properties of the hearing protector device 9 can be achieved, thus the hearing protector device 9 can be adapted to a different application. Additionally, the alteration may also limit the number of active components in the overall system making it more user-friendly.

Modifications and other variants of the described embodiments will come to mind to one skilled in the art having benefit of the teachings presented in the foregoing description and associated drawings. Therefore, it is to be understood that the embodiments are not limited to the specific example embodiments described in this disclosure and that modifications and other variants are intended to be included within the scope of this disclosure. Furthermore, the presented exemplary use cases are in no way intended as limiting, but simply as means to further exemplify how present invention can be used in different applications. As used herein, the terms "comprise/comprises" or "include/includes" do not exclude the presence of other elements or steps. Furthermore, although individual features may be included in different claims (or embodiments), these may possibly advantageously be combined, and the inclusion of different claims (or embodiments) does not imply that a certain combination of features is not feasible and/or advantageous. In addition, singular references do not exclude a plurality. Finally, reference signs in the claims are provided merely as a clarifying example and should not be construed as limiting the scope of the claims in any way.

The invention claimed is:

1. A hearing protector device comprising a controller, a memory, and a receiver; at least one stored signal parameter and at least one suitable notification being stored in said memory; said at least one suitable notification being associated with said at least one stored signal parameter; wherein the controller is configured to be connected to the memory, the receiver, and at least one user-notifying device adapted to notify a hearing protector user of a change in an environment or vicinity around the hearing protector user or a change in a parameter of a tool or machine being used by the worker and to notify the hearing protector user of such change;
   wherein the hearing protector device is configured to receive at least one data transmission signal from a data transmission device; said data transmission signal being indicative of said change;
   the controller being configured to compare said data transmission signal to said at least one stored signal parameter;
   wherein the user-notifying device is configured to, when the signal from the data transmission device matches the stored signal parameter, present the at least one suitable notification associated with the signal parameter to the hearing protector user to notify the hearing protector user of the change; said suitable notification being different from said change.

2. The hearing protector device according to claim 1, configured to receive the data device signal, said data device signal comprising identification data associated with at least one external source generating at least one external signal which the data transmission device is configured to receive, wherein said data device signal is generated by the data transmission device.

3. The hearing protector device according to claim 1, wherein said hearing protector device is configured to for each successful matching of the data transmission signal and stored signal parameter generate signal detection data and storing said signal detection data.

4. The hearing protector device according to claim 1, configured to receive preconfigured notifications and/or signal parameters from an external device.

5. The hearing protector device according to claim 1, further comprising a storing switch configured to upon activation enable an active data transmission signal to be stored in the hearing protector device as a stored signal parameter.

6. The hearing protector device according to claim 1, further comprising at least one sensor adapted to collect data concerning at least one parameter.

7. The hearing protector device according to claim 1, further comprising more than one user-notifying device, said user-notifying devices being configured to be operated independently of each other.

8. The hearing protector device according to claim 1, wherein the at least one user-notifying device comprises a speaker adapted to send notifications to the hearing protector user in the form of audio.

9. The hearing protector device according to claim 1, wherein the at least one user-notifying device comprises a tactile device configured to send notifications to the hearing protector user in the form of tactile signals.

10. The hearing protector device according to claim 1, wherein the hearing protector device is an active noise cancelling hearing protector.

11. The hearing protector device according to claim 1, further configured to receive an encrypted data transmission signal and decrypting said signal.

12. The hearing protector device according to claim 1, further comprising a media playing device, wherein said media playing is configured to communicate with the controller and accentuate the notifications.

13. The hearing protector device according to claim 1, wherein the data transmission device comprising comprises a processor configured to be connected to an external signal receiver, a data device transmitter;
   wherein the data transmission device is configured to receive at least one external signal from an external source and transmit said data transmission signal which is configured to be received by said hearing protector device; said data transmission signal containing information indicative of the external signal received by the external signal receiver and being indicative of a change in an environment or vicinity around the hearing protector device or a change in a parameter of a tool or machine being used by the user of the hearing protector device.

14. The data transmission device according to claim 13, further configured to generate identification data associated with the external signal and/or external source and transmit the data transmission signal comprising the identification data.

15. The data transmission device according to claim 13, wherein the data transmission device further comprises an inter-linking device configured to communicatively couple said data transmission device to at least one second data transmission device configured to receive additional external signals.

16. A user notifying system comprising a data transmission device and a hearing protector, said hearing protector being configured to be worn by a user;
   said data transmission device comprising an external signal receiver, a processor, and a transmitter; whereby, which external signal receiver senses an environmental parameter desired to be monitored and transmits said external signal to said processor; said processor controlling said transmitter to transmit a data signal containing information indicative of the sensed parameter; and
   said hearing protector comprising a receiver which receives the data signal from said data transmission device, a memory in which is stored at least one stored signal parameter and at least one suitable notification, a controller, and a transmitter; said at least one suitable notification being associated with said at least one stored signal parameter and being different from said environmental parameter being monitored; said controller being adapted to compare said data signal with said at least one stored parameter, and, if there is a match, said controller controls said transmitter to issue said at least one notification associated with said parameter.

* * * * *